United States Patent
Gellman et al.

(10) Patent No.: US 9,034,309 B2
(45) Date of Patent: May 19, 2015

(54) BIOCIDAL POLYMERS

(75) Inventors: Samuel H. Gellman, Madison, WI (US);
Michael A. Gelman, Madison, WI (US);
Bernard Weisblum, Madison, WI (US);
David M. Lynn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 2461 days.

(21) Appl. No.: 10/933,987

(22) Filed: Sep. 3, 2004

(65) Prior Publication Data

US 2005/0079150 A1    Apr. 14, 2005

Related U.S. Application Data

(60) Provisional application No. 60/500,201, filed on Sep. 4, 2003.

(51) Int. Cl.
| | |
|---|---|
| A61K 31/74 | (2006.01) |
| C08L 51/00 | (2006.01) |
| C08F 257/02 | (2006.01) |
| C08F 265/04 | (2006.01) |
| C08F 265/10 | (2006.01) |
| C08F 283/06 | (2006.01) |
| C08G 65/04 | (2006.01) |
| C08G 65/329 | (2006.01) |
| C08L 25/04 | (2006.01) |
| C08L 33/08 | (2006.01) |
| C08L 33/26 | (2006.01) |
| C08L 35/06 | (2006.01) |
| C08L 55/00 | (2006.01) |
| C08L 59/04 | (2006.01) |

(52) U.S. Cl.
CPC .............. *C08L 51/003* (2013.01); *A61K 31/74* (2013.01); *C08F 257/02* (2013.01); *C08F 265/04* (2013.01); *C08F 265/10* (2013.01); *C08F 283/06* (2013.01); *C08G 65/04* (2013.01); *C08G 65/329* (2013.01); *C08L 25/04* (2013.01); *C08L 33/08* (2013.01); *C08L 33/26* (2013.01); *C08L 35/06* (2013.01); *C08L 55/00* (2013.01); *C08L 59/04* (2013.01)

(58) Field of Classification Search
USPC ...................................... 424/78.08
See application file for complete search history.

(56) References Cited

U.S. PATENT DOCUMENTS

| | | | | |
|---|---|---|---|---|
| 2,802,812 | A | * | 8/1957 | Overberger .................... 526/346 |
| 3,520,970 | A | * | 7/1970 | Klaus et al. .................... 424/482 |
| 4,482,680 | A | | 11/1984 | Sheldon et al. |
| 4,826,924 | A | | 5/1989 | Kourai et al. |
| 5,015,464 | A | * | 5/1991 | Strobridge ....................... 424/48 |
| 5,348,738 | A | * | 9/1994 | Takatsuka et al. .......... 424/78.37 |
| 5,607,663 | A | * | 3/1997 | Rozzi et al. ...................... 424/49 |
| 5,683,709 | A | * | 11/1997 | Yamada et al. ................ 424/409 |
| 6,020,491 | A | | 2/2000 | Wonley et al. |
| 6,482,402 | B1 | | 11/2002 | Kurtz et al. |
| 2002/0102369 | A1 | * | 8/2002 | Shimizu et al. ............... 428/1.33 |
| 2003/0113291 | A1 | | 6/2003 | Schmidt et al. |

FOREIGN PATENT DOCUMENTS

EP    0 952 168 A    10/1999

OTHER PUBLICATIONS

Gelman et al. "Biocidal Activity of Polystyrenes That Are Cationic by Virtue of Protonation". Organic Letters. 2004. vol. 6. No. 4. pp. 557-560.*
Se, K. "Anionic Living Polymerization of tert-Aminostyrenes and Application of the Polymers". Polymers for Advanced Technologies. 2003. vol. 14. pp. 177-183.*
Panarin (Pharmaceutical Chemistry Journal, vol. 5 No. 7 (1971) pf 406-408).*
Arvidsson,et al..(2001) On the Antimicrobial and Hemolytic Activities of Amphiphilic β-Peptides, *ChemBioChem* 2001, 2, 771-773.
Auzanneau et al. (1998) Synthesis and characterization of polyethylene glycol polyacrylamide copolymer (PEGA) resins containing carbohydrate ligands. Evaluation as supports for affinity chromatography., *Can. J. Chem.* 76(8):1109-1118.
Bessalle, et al., (1990), All-D-magainin: chirality, antimicrobial activity and proteolytic resistance, *FEBS Lett.*, 274, 151-155.
Cavagnero et al. (1995), Response of Rubredoxin from *Pyrococcus furiosus* to Environmental Changes: Implications for the Origin of Hyperthermostability, *Biochemistry* 34:9865-0873.
Chen et al., (1988), Synthetic magainin analogues with improved antimicrobial activity, *FEBS Lett.* 236, 462-466.
Chen et al., (2000), Quarternary Ammonium Funtionalized Poly(propylene imine) Dendrimers as Effective Antimicrobials: Structure-Activity Studies, *Biomacromolecules* 1, 473-480.
Cheng et al., (2001), β-Peptides: From Structure to Function, *Chem. Rev.* (Washington, D. C.), 101, 3219-3232.
Cheng et al., (Feb. 2003), Synthesis of block copoly(polyethylene glycol-styrene) by the macromonomer and macroinitiator method, *Materials Chemistry & Physics* 78(3):581-590.
Denisov et al., "Handbook of Free Radical Initiators," © 2003, Wiley, New York, NY; ISBN 0-471-20753-5.
Doddrell et al., (1982), Distortionless Enhancement of NMR Signals by Polarization Transfer. J. Magn. Res., 48, 323-327.
Gademann et al., (1999) β-Peptdes: Twisting and Turning, *Curr. Med. Chem.*, 6, 905-925.

(Continued)

*Primary Examiner* — Benjamin Packard
(74) *Attorney, Agent, or Firm* — Daniel A. Blasiole; Joseph T. Leone, Esq.; DeWitt Ross & Stevens

(57) ABSTRACT

Pharmaceutical compositions containing biocidal co-polymers of poly(styrenes), poly(acrylates), poly(acrylamides), and poly($C_1$-$C_6$)alkylene glycols are disclosed, along with methods of using the compositions to treat microbial infections in mammals.

15 Claims, No Drawings

(56) References Cited

OTHER PUBLICATIONS

Giangaspero et al., (2001), Amphipathic α helical antimicrobial peptides, A Systematic study of the effects of structural and physical properties on biological activity, (2001), *Eur J Biochem*, 268, 5589-5600.

Hamuro et al., (1999), De Novo Design of Antibacterial β-Peptides, *J. Am. Chem. Soc.*, 121, 12200-12201.

Ikeda et al., (1983), Synthesis and antimicrobial activity of poly(trialkylvinylbenzylammonium chloride)s,. *Makromol. Chem., Rapid Commun.*, 4, 459-461.

Ikeda, T.; Tazuke, S.; Suzuki, Y., Synthesis and antimicrobial activity of poly(trialkylvinylbezylammonium chloride)s, *Makromol. Chem.* 1984, 185, 869-876.

Ishizu et al., (Mar. 2000), Radical copolymerization reactivity of methacryloyl-terminated poly(ethylene glycol methylether) with vinylbenzyl-terminated polystyrene macromonomers, *Polymer*, 41(6):2053-2057.

Kawabata et al., (1988), Antibacterial Activity of Soluble Pyridinium-Type Polymers, *Appl. and Environ. Microbiology*, 54(10):2532-2535.

Li et al., (1998), Study of Pyridinium-Type Functional Polymers. II. Antibacterial Activity of Soluble Pyridinium-Type Polymers. *J. Appl. Polym. Sci.*, 67, 1761-1768.

Lin, J.; Qiu, S.; Lewis, K.; Klibanov, A. M., Bactericidal Properties of Flat Surfaces and Nanoparticles Derivatized with Alyylated Polyethylenimines, *Biotechnol. Prog.* 2002, 18, 1082-1086.

Liu et al., (2001), De Novo Design, Synthesis, and Characterization of Antimicrobial β-Peptides, *J. Am. Chem. Soc.*, 123, 7553-7559.

Matsuzaki et al., (1997), Modulation of Magainin 2-Lipid Bilayer Interactions by Peptide Charge, *Biochemistry*, 36, 2104-2111.

Matsuzaki et al., (1997), Interactions of an antimicrobial peptide, magainin 2, with outer and inner membranes of Gram-negative bacteria, *Biochim. Biophys. Acta*, 1327, 119-130.

Merrifield et al., (1995), Retro and retroenantio analogs of cecropin-melittin hybrids, *Proc. Natl. Acad. Sci. U.S.A.*, 92, 3449-3453.

Nicas et al., (1989), Characterization of Vancomycin Resistance in *Enterococcus faecium* and *Enterococcus faecalis*, *Antimicrob. Agents Chemother.*, 33, 1121-1124.

Oh et al., (1986), Copolymerization Reactivity Ratios of p. Vinylbensophenone and p. Dimethylamino Styrene,. *J. Polym. Sci.*, Part C: Polym. Lett., 24, 229-232.

Ohta et al., (2001), A Comparative Stud of Characteristics of Current-Type and Conventional-Type Cationic Bactericides, *Biol. Pharm. Bull.*, 24, 1093-1096.

Oren et al., (1997). A Repertoire of Novel Antibacterial Diastereomeric Peptides with Selective Cytolytic Activity, *J. Biol. Chem.*, 272, 14643-14649.

Oren et al., (2000), Cyclization of a Cytolytic Amphipathic α-Helical Peptide and Its Diastereomer: Effect on Structure, Interaction with Model Membranes, and Biological Function, *Biochemistry*, 39, 6103-6114.

Porter et al., (2002), Mimicry of Host-Defense Peptides by Unnatural Oligomers: Antimicrobial β-Peptides, *J. Am. Chem. Soc.*, 124, 7324-7330.

Porter et al., (2000), Non-haemolytic β-amino-acid oligomers, *Nature* (London, U.K.), 404, 565.

Raguse et al., (2002) Structure—Activity Studies of 14-Helical Antimicrobial β-Peptides: Probing and Relationship between Conformational Stability and Antimicrobial Potency. *J. Am. Chem. Soc.*, 124, 12774-12785.

Semisotnov et al., (1991), Study of the "Molten Globule" Intermediate State in Protein Folding by a Hydrophobic Fluorescent Probe, *Biopolymers* 31:119-128.

Senuma et al., (1989), Synthesis and Antibacterial Activity of Copolymers Having a Quaternary Ammonium Salt Side Group, *J. Appl. Polym. Sci.*, 37, 2837-2843.

Senuma et al., (1993), Antibacterial activity of copolymers of trialkyl(4-vinylbenzyl)ammonium chlorides with acrylonitrile, *Angew. Makromol. Chem.*, 204, 119-125.

Sheldon et al., (1983), Quaternary Ammonium Group-Containing Polymers Having Antimicrobial Activity, In PCT Int. Appl.; (Dynapol, USA). Wo, p. 30 pp.

Stone, (2002), Microbicides: A New Approach to Preventing HIV and Other Sexually Transmitted Infections, A. Nat. Rev. Drug Discovery, 1, 977-985.

Tew et al., (2002), De Novo design of biomimetic antimicrobial polymers, *Proc. Natl. Acad. Sci. U.S.A.*, 99, 5110-5114.

Tiller et al., (201), Designing surfaces that kill bacteria on contact, *Proc. Natl. Acad. Sci. U.S.A.*, 98, 5981-5985.

Tossi et al., (2000), Amphipathic, α-Helical Antimicrobial Peptides, *Biopolymers*, 55, 4-30.

Vucetic, J. J.; Vandjel, V. H.; Janic, M. D. *Glas. Hem. Drus. Beograd* 1977, 42, 389-391.

Wade et al., (1990), All-D amino acid-containing channel-forming antibiotic peptides, *Proc. Natl. Acad. Sci. U.S.A.*, 87, 4761-4765.

Wieprecht et al., (1997), Peptide Hydrophobicity Controls the Activity and Selectivity of Magainin 2 Amide in Interaction with Membranes, *Biochemistry*, 36, 6124-6132.

Yanisch-Perron et al., (1985), Improved M13 phage cloning vectors and host strains: nucleotide sequences of the M13mp18 and pUC19 vectors, *Gene*, 33, 103-119.

Yau et al., "Modern size-exclusion liquid chromatography; practice of gel permeation and gel filtrationchromatography," © 1979, Wiley: New York, NY.

Young et al., (1969), Chromosomal Location of Genes Regulating Resistance to Bacteriophage in *Bacillus subtilis*, *J. Bacteriol.*, 98, 1087-1097.

Zasloff et al., (2002), Antimicrobial peptides of multicellular organisms, *Nature* (London, U.K.), 415, 389-395.

\* cited by examiner

BIOCIDAL POLYMERS

CROSS-REFERENCE TO RELATED APPLICATIONS

This application claims priority under 35 USC §119(e) to U.S. Provisional Application Ser. No. 60/500,201, filed 4 Sep. 2003, the entirety of which is incorporated herein.

FEDERAL FUNDING

This invention was made with United States government support awarded by the following agencies: NSF 0140621. The United States has certain rights in this invention.

INCORPORATION BY REFERENCE

All of the references cited below are incorporated herein by reference.

FIELD OF THE INVENTION

The invention is directed to pharmaceutical compositions containing biocidal co-polymers of poly(styrenes), poly(acrylates), poly(acrylamides), and poly($C_1$-$C_6$)alkylene glycols. More specifically, the invention is directed to pharmaceutical compositions and methods of treating microbial infections in mammals.

BACKGROUND

The emerging prevalence of bacteria resistant to common therapeutic agents has led to a dire need for new antimicrobial compounds.[1] Peptide antimicrobials,[2] a central element of the human immune system, have received increasing interest as potentially new antimicrobial treatments. One reason for their potential success is that it appears to be difficult, although not impossible, for pathogenic microbes to develop resistance to these innate "host-defense" peptides. One large subset of host-defense peptides forms an amphiphilic α-helical structure. These peptides act by disrupting bacterial membranes because their net positive charge attracts the peptides to the negatively charged bacterial membrane,[4] and the hydrophobic face of the helix allows the formation of aggregates that compromise membrane integrity.[2] Amphiphilic topology also plays a factor in the biological activity of these molecules, as enantiomeric peptides retain full activity.[5]

This design principle has been applied to distinct types of amphiphilic helical antimicrobial oligomers. For example, β-Amino acid oligomers ("β-peptides") can adopt discrete helical conformations.[6] By properly arranging cationic and lipophilic residues within the β-peptide, amphiphilic helices with antimicrobial activity can by obtained.[7-9] DeGrado et al. also describe aryl amide oligomers with elongated conformations that can project lipophilic and cationic groups to opposite sides of the molecular backbone.[10] Unlike α- or β-peptide oligomers, these aryl amide oligomers are achiral.

SUMMARY OF THE INVENTION

The invention disclosed and claimed herein arose from the inventors' interest in determining how much conformational "pre-organization" is required for antimicrobial activity in synthetic oligomers or polymers. For example, the helical, antimicrobial β-peptides developed by Gellman et al. are composed of cyclically-constrained β-amino acids and are quite rigid.[8,9] As a result, antimicrobial activity is generally attenuated or lost entirely upon sequence scrambling to give a non-amphiphilic helix.[9] In contrast, α-helical host-defense peptides composed of α-amino acid residues can be scrambled with only modest loss of activity.[11] This difference in the effect of residue scrambling can be explained by invoking the increased flexibility of the α-peptide backbone, which might allow scrambled sequences to populate non-helical, but globally amphiphilic, conformations. The highly preorganized β-peptide backbone cannot adopt such non-helical conformations. While this mechanistic theory appears to explain the difference in activity observed between α-peptides and β-peptides, Applicants are not limiting their invention to any specific mechanistic pathway.

Extending this hypothesis, the present inventors postulate that any sufficiently flexible synthetic polymer backbone might display a random sequence of cationic and lipophilic side-chains in a manner that results in global amphiphilicity and, therefore, biocidal activity in general and antimicrobial activity in particular. This hypothesis was put to the test by directly comparing cationic polystyrene-based polymers to an α-peptide known to display potent antimicrobial activity. Polystyrenes were chosen as a test backbone. Other polymeric species, such as poly(alkylene glycols) (e.g., poly(ethylene glycol)) and poly(acrylates) are also included within the scope of the present invention. Polystyrene derivatives are preferred.

The present invention, therefore, is drawn to a new class of biocidal and antimicrobial polymers in which a poly(styrene), a poly(acrylamide), a poly(acrylate), or a poly($C_1$-$C_6$-alkylene glycol) backbone is combined with side-chains that require protonation for positive charge. The results represent the first direct comparison between an antimicrobial α-peptide and synthetic polymers. As shown by the Examples presented below, styrene copolymers can display biocidal activity comparable to that of a modified host-defense peptide. This result supports the hypothesis that backbone "pre-organization" is not essential for potent biocidal and antimicrobial activity.[27]

DETAILED DESCRIPTION OF THE INVENTION

Abbreviations and Definitions

The following abbreviations are used through the specification and claims:

AIBN=2,2'-azo-bis-isobutyrylnitrile, a free-radical polymerization initiator

ANS=the dye 4-aminonaphthalene-1-sulphonic acid

BHI=brain-heart infusion broth

DEPT-135=Distortionless Enhancement by Polarization Transfer. In $^{13}$C NMR, the DEPT technique enables carbon atoms to be assigned according to the number of attached protons. The DEPT-135 technique shows —CH3 and —CH— carbons as having positive phase and —CH$_2$— carbons as having negative phase. Quaternary carbons do not appear in the DEPT technique. See, for example, Doddrell, et al.[28]

DMAS=4-(dimethylaminomethyl)-styrene (compound 1)

GPC=gel permeation chromatography

Initiator=a compound capable of initiating free-radical polymerization. A host of initiators are known in the art and include azo compounds (e.g., AIBN), dialkyl and diacyl per-oxides, hydroperoxides, peresters, and organic polyoxides. AIBN is preferred. Initiators are widely available commercially, such as from DuPont (marketed as "VAZO"-brand free radical initiators, Wilmington, Del.) and from Aldrich Fine Chemicals (Milwaukee, Wis.). Exemplary initiators include, without limitation, t-amyl peroxybenzoate, 4,4-azo-bis-(4-cyanovaleric acid), 1,1'-azo-bis-(cyclohexanecarbonitrile), AIBN, benzoyl peroxide, 2,2-bis-(t-butylperoxy)butane, 1,1-bis-(t-butylperoxy)cyclohexane, 2,5-bis-(t-butylperoxy)-2,5-dimethylhexane, 2,5-bis-(t-butylperoxy)-2,5-dimethyl-3-hexyne, t-butyl-peracetate, t-butyl peroxide, t-butyl peroxybenzoate, t-butylperoxy-isopropyl carbonate, cumene hydroperoxide, peracetic acid, potassium persulfate, and the like. See Denisov et al.[29] for an exhaustive treatment of free-radical initiators and free-radical-mediated polymerizations.

MBC=minimal bactericidal concentration; the minimum concentration of an active agent that kills all or substantially all of the selected target cell type.

MIC=minimum inhibitory concentration; the minimum concentration of an active agent that inhibits growth of the selected target cell type.

NMR=nuclear magnetic resonance spectroscopy

PDI=polydispersity index

Pharmaceutically-suitable salt: any salt conventionally used in the formulation of pharmaceutical compositions for ingestion, injection, or topically application, including, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like; and base addition salts, including those derived from alkali or alkaline earth metal bases or conventional organic bases, such as triethylamine, pyridine, piperidine, morpholine, N-methylmorpholine, and the like.

UV-Vis=ultraviolet-visible spectroscopy

Biocidal and Antimicrobial Pharmaceutical Compositions

The biocidal and antimicrobial compositions of the present invention contain as active ingredients co-polymers of poly (styrenes), poly(acrylates), poly(acrylamides), and poly($C_1$-$C_6$-alkylene glycols). Co-polymers of poly(styrenes) are preferred. Copolymers of 4-(dimethylaminomethyl)-styrene (1) and 4-octylstyrene (2) were prepared by a free-radical polymerization method.[12] Hydrophobic size-exclusion chromatography using Sephadex LH-20 yielded samples of polymer without monomer vinyl peaks in the $^1$H NMR spectrum. For clarity and brevity, copolymers will be referred to herein by the molar percentages of monomers in the feed mixture. Thus, copoly($1_{95}$:$2_5$) refers to the product generated by polymerization of a mixture of 95 mol % 1 and 5 mol % 2. Analysis of the copolymers indicated that their composition closely approximates that of the feed mixture.[13]

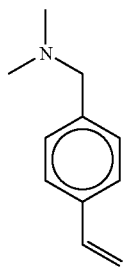

1

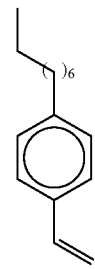

2

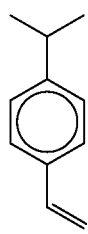

3

4

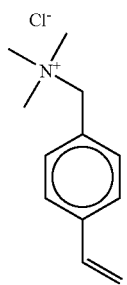

5

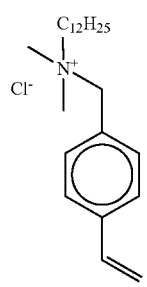

6

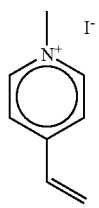

Polymer molecular weight averages were determined by GPC using literature methods.[14] Most polymers had molecular weights (Mw) close to 9000 Da, with polydispersity indices, PDI's (i.e., Mw/Mn) close to 3.0, which is typical for AIBN-initiated radical polymerizations. These data yield Mn values near 3000, which are comparable to the molecular weight of the magainin derivative used as a standard (MW=2478). A chromatographic assay demonstrated that these materials were in fact copolymers of 1 and 2 and not simply mixtures of polymers formed from the homopolymerization of 1 and 2.[14]

Thus, the present invention is directed to biocidal and antimicrobial pharmaceutical compositions (homopolymers and heteropolymers), wherein the active ingredient comprises one or more polymers of the formula $-(A)_n-$, wherein each A is a residue independently selected from the group consisting of:

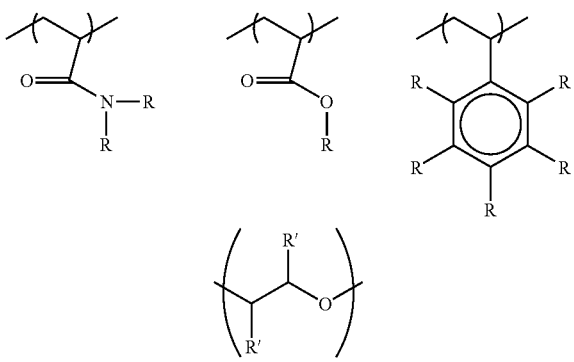

wherein each R is independently selected from the group consisting of hydrogen, linear or branched $C_1$-$C_{30}$-alkyl, alkenyl, or alkynyl, unsubstituted amino-$C_1$-$C_6$-alkyl, mono-substituted amino-$C_1$-$C_6$-alkyl, disubstituted amino-$C_1$-$C_6$-alkyl, mono- or bicyclic aryl, mono- or bicyclic heteroaryl having up to 5 heteroatoms selected from N, O, and S; mono- or bicyclic aryl-$C_1$-$C_6$-alkyl, mono- or bicyclic heteroaryl-$C_1$-$C_6$-alkyl, $-(CH_2)_{n+1}-OR^1$, $-(CH_2)_{n+1}-SR^1$, $-(CH_2)_{n+1}-S(=O)-CH_2-R^1$, $-(CH_2)_{n+1}-S(=O)_2-CH_2-R^1$, $-(CH_2)_{n+1}-NR^1R^1$, $-(CH_2)_{n+1}-NHC(=O)R1$, $-(CH_2)_{n+1}-NHS(=O)_2-CH_2-R^1$, $-(CH_2)_{n+1}-O-(CH_2)_m-R^2$, $-(CH_2)_{n+1}-S-(CH_2)_m-R^2$, $-(CH_2)_{n+1}-S(=O)-(CH_2)m-R^2$, $-(CH_2)_{n+1}-S(=O)_2-(CH_2)_m-R^2$, $-(CH_2)_{n+1}-NH-(CH_2)_m-R^2$, $-(CH_2)_{n+1}-N-\{(CH_2)_m-R^2\}_2$, $-(CH_2)_{n+1}-NHC(=O)-(CH_2)_{n+1}-R^2$, and $-(CH_2)_{n+1}-NHS(=O)_2-(CH_2)_m-R^2$;

wherein $R^1$ is independently selected from the group consisting of hydrogen, $C_1$-$C_6$-alkyl, alkenyl, or alkynyl; mono- or bicyclic aryl, mono- or bicyclic heteraryl having up to 5 heteroatoms selected from N, O, and S; mono- or bicyclic aryl-$C_1$-$C_6$-alkyl, mono- or bicyclic heteroaryl-$C_1$-$C_6$-alkyl; and wherein $R^2$ is independently selected from the group consisting of hydroxy, $C_1$-$C_6$-alkyloxy, aryloxy, heteroaryloxy, thio, $C_1$-$C_6$-alkylthio, $C_1$-$C_6$-alkylsulfinyl, $C_1$-$C_6$-alkylsulfonyl, arylthio, arylsulfinyl, arylsulfonyl, heteroarylthio, heteroarylsulfinyl, heteroarylsulfonyl, amino, mono- or di-$C_1$-$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$-$C_6$-alkylamino, carboxylic acid, carboxamide, mono- or di-$C_1$-$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, sulfonic acid, sulfonamide, mono- or di-$C_1$-$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$-$C_6$-alkyl, aryl, heteroaryl; O-alkylurethane, O-arylurethane, and O-heteroarylurethane;

wherein $R^1$ is selected from same group recited above for R, provided that one of $R^1$ is hydrogen;

wherein n is an integer≥3 (preferably ≥6);

provided that at least one "A" is a nitrogen-containing residue wherein the nitrogen atom is capable of being protonated;

and pharmaceutically-suitable salts thereof, in combination with a pharmaceutically-suitable carrier.

Note that where a substituent is designated as being "independently selected" from a given set of moieties, each appearance of the stated substituent can be different. Thus, for example, the formula $-(A)_n-$ comprises homopolymers wherein each appearance of "A" is the same, and heteropolymers where each appearance of "A" is different (i.e., A-A'-A'''-A'''). The same applies for the various R substituents.

Synthesis of the poly(styrene), poly(acrylamide), and poly(acrylate) co-polymers according to the present invention is preferably carried out via free-radical-mediated polymerization, as described in the Examples.

While poly($C_1$-$C_6$-alkylene glycol) co-polymers can by synthesized using free-radical methods, it is not the preferred route. Using poly(ethylene glycol) (PEG) as an example, PEG is preferably synthesized via a ring-opening reaction of ethylene oxide, which is widely known in the art. Poly(alkylene glycol) can be co-polymerized with the other monomer types described herein using the methods described in, for example, Ishizu, Shen & Tsubaki (March 2000) *Polymer*, 41(6):2053-2057, and Cheng, Wang & Chen (February 2003) *Materials Chemistry & Physics* 78(3):581-590. For methods of synthesizing co-polymers of PEG and poly(acrylamides), see Auzanneau et al. (1998) *Can. J Chem.* 76(8):1109-1118.

Ring-opening polymerizations of epoxides, such as ethylene oxide or propylene oxide may be accomplished using cationic ring-opening polymerization. Strong protic acids are conventionally used as a catalyst, e.g., $H_2SO_4$, $CF_3SO_3H$, and $CF_3CO_2H$. The same polymerization can also be accomplished using anionic ring-opening polymerization. Typical initiators for anionic ring-opening polymerization include, without limitation, alkali metals (Na, K), inorganic bases (NaOH, KOH), metal oxides ($LiOCH_3$), and metal alkyls and hydrides (BuLi, NaH).

Polymerization can be head-to-tail and/or head-to-head, syndiotactic, isotactic, and combinations thereof Polymers that are cationic by virtue of quaternized nitrogen atoms and structurally related to poly(1) and copoly(1:2) have been studied as antimicrobial agents.[14-18] However, polymers prepared from 1 differ significantly from the quaternized prior art compounds in that, like host-defense peptides, polymers containing dimethylaminomethyl groups require protonation to develop positive charge. Thus, the preferred compounds for use in the present invention are those containing a fraction (e.g., from about 1 mol % to about 99 mol %) of R groups that require protonation to develop positive charge, and a fraction that or R groups (e.g., from about 99 mol % to about 1 mol %) that are neutral or anionic.

Two examples from the quaternized class of compounds were used for comparison with the protonatable polymers described herein. Poly(5) was synthesized from monomer 5 via reported methods.[16,19] Poly(7) was purchased (Sigma, St. Louis, Mo.) in a form that is >98% quaternized, having an Mn=12.0 KDa and a PDI=1.06. Both poly(5) and poly(7) are quaternized via N-methylation. These polymers have shorter alkyl chains than the octyl group of (2) but are preferred for this work because limited aqueous solubility was reported by Senuma et al. for the N-dodecyl analogue of poly(5)[18] and by Lin et al. for the N-hexyl analogue of poly(7).[20]

Minimum inhibitory concentrations (MICs) for poly(1) and the copoly(1:2) series were determined against $E.$ $Coli,$[21] $B.$ $subtilis,$[22] methicillin-resistant $S.$ $aureus$[23] (MRSA), and vancomycin-resistant $E.$ $faecium$[24] (VRE). Assays were conducted at polymer concentrations up to 50 µg/mL. Most polymers were not tested at higher concentrations due to limited solubility in the assay media. The data given are conservative estimates of MIC because some precipitation occurred (at concentrations above 12.5 µg/mL) over the 6-hour incubation period, thus causing turbidity even in the absence of bacteria. A high-activity magainin analogue, (Ala$^{8,3,18}$)-magainin-2-amide,[25] was used as a positive control.

The tertiary amine-containing polymers show inhibitory activity similar to that of the magainin against all four organisms tested. Monomer 1 showed no growth inhibition. Poly (5) was inactive in all experiments except one, inhibiting $B.$ $subtilis$ at 50 µg/mL. Past assays of poly(5) used agar plate assays,[15,18,19] which are prone to artifacts due to interaction of the polymers with the agar,[16] or cell viability counting after incubating cells with polymer in sterile water or saline.[16] The poor activity of poly(5) in our brain-heart infusion broth (BHI) growth inhibition assay could be due to interaction with anionic components of the broth.[16] Methylpyridinium-bearing poly(7) showed some inhibition for three strains. This moderate activity is comparable to that observed by Lin et al. for poly(7) of tenfold higher molecular weight.[20]

TABLE 1

Minimum Inhibitory Concentrations (MIC's, µg/mL) for polymers vs. the four bacterial strains tested. Subscripts refer to mole fraction of monomer.

| Strain | E. coli JM109 | B. subtilis BR151 | S. aureus 5332 | E. faecium A436 |
|---|---|---|---|---|
| poly(1) | 25 | 12.5 | 50 | 12.5 |
| Copoly($1_{97}$:$2_3$) | 50 | 12.5 | 25 | 6.3 |
| Copoly($1_{95}$:$2_5$) | 50 | 12.5 | 25 | 6.3 |
| copoly($1_{93}$:$2_7$) | 25 | 6.3 | 12.5 | 3.2 |
| copoly($1_{90}$:$2_{10}$) | 50 | 12.5 | 17.8 | 6.3 |
| copoly($1_{85}$:$2_{15}$) | 50 | 25 | 25 | 12.5 |
| copoly($1_{80}$:$2_{20}$) | 50 | 35.4 | 25 | 25 |
| copoly($1_{70}$:$2_{30}$) | >50 | 50 | >50 | 50 |
| copoly($1_{65}$:$2_{35}$) | >50 | >50 | >50 | 50 |
| (Ala$^{8,3,18}$)-magainin-2-amide | 12.5 | 6.3 | 12.5 | 3.2 |
| poly(5) | >50 | 50 | >50 | >50 |
| poly(7) | >50 | 25 | 35.4 | 50 |
| (1) (monomer) | >50 | >50 | >50 | >50 |

Both nonpolar and electrostatic forces are believed to be important in the interactions of host-defense peptides with bacterial membranes.[26] Prior studies of copolymers of vinylbenzylammonium[18,19] and vinylpyridinium[17] salts have shown that antimicrobial activity is influenced by the proportion of cationic and lipophilic monomers. In an examination of N-benzyl-4-vinyl pyridinium/styrene copolymers, Li et al. found that sterilizing activity at first remained constant as the proportion of styrene was raised; once a threshold value was reached, however, additional styrene incorporation led to decreased activity.[17] The present data for copoly(1:2) show a related pattern. Below 20-30% (2), antimicrobial activity is only modestly affected by the proportion of lipophilic component (2), but above this level activity drops precipitously.

GPC analysis showed that for the polymers described in the Examples, the GPC procedure used gives similar, broad molecular weight distributions, regardless of polymer composition, a phenomenon typical of AIBN-initiated free-radical polymerizations.

These polymers contain both hydrophobic and hydrophilic functionality. Their hydrophobic portions could be either buried within micelle-like structures or exposed to solvent. Colorimetric assays, as described in the Examples, were performed to test each of these hypotheses. Specifically, solubilization of the hydrophobic dye Orange OT can indicate the formation of micelle-like structures with hydrophobic interior regions. Single polymer molecules might form such structures even at low concentrations, but the data collected to date (not shown) did not show significant, reproducible dye solubilization. Hence, at the concentrations studied, the subject polymers do not act as conventional micellar detergents.

The dye 4-anilinonaphthalene-1-sulfonic acid (ANS) shows a drastic increase in fluorescence on binding solvent-exposed hydrophobic patches in the "molten globule" state of proteins. See Cavagnero et al. (1995) Biochemistry 34:9865-0873, and Semisotnov et al. (1991) Biopolymers 31:119-128. Fluorescence also correlates to the amount of exposed hydrophobic surface displayed by poly(amino acid)s. When polymers were excited at 350 nm to avoid fluorescence from the aromatic polymers themselves, significant enhancement of ANS fluorescence was seen, suggesting exposure of hydrophobic surface, but no correlation was evident with polymer composition.

The data on Orange OT solubilization and ANS fluorescence, taken together, are consistent with a "molten globule-like" model of polymer conformation. In such a model, these polymers cannot present solely cationic functionality to the solvent surface at the concentrations studied.

The tertiary amine-containing polymers show inhibitory activity against all four organisms tested. Because data points are taken at twofold dilutions, a twofold variation in MIC corresponds to a single data point. Therefore, even the apparently wide variation in MIC seen should be interpreted with great caution.

The polymers also show bactericidal activity against both Gram-positive and Gram-negative pathogens.

The interaction between anionic bacterial membranes and antimicrobial peptides is believed to be primarily electrostatic. Nevertheless, poly(1) and its derivatives displayed antibacterial activity similar to that of magainin, whereas poly(5) and poly(6) showed little to no activity.

Past assays of poly(5) and poly(6) used agar plate assays (which have since been discredited) or cell viability counting after incubating cells with polymer in sterile water or saline. The low activity of the comparison polymers in the BHI growth inhibition assay may be due to interaction between the polymers and anionic components of the broth. However, a rich medium like BHI may better represent conditions encountered during infection of a host organism.

All of the tertiary amine polymers described in the Examples are useful as broad-spectrum biocides and antiseptics.

Pharmaceutical compositions of the present invention, comprise a biocidal- or antimicrobial-effective amount of an active compound as described above, an isomeric form thereof, or a pharmaceutically acceptable salt of the compound or isomeric form thereof, together with an acceptable carrier for it, and optionally other therapeutically active ingredients. The carrier must be "pharmaceutically acceptable" or "pharmaceutically suitable," i.e., the carrier must be compatible with the other ingredients of the composition and not deleterious to the recipient thereof.

The compositions include those suitable for oral, rectal or parenteral (including subcutaneous, intramuscular, intradermal and intravenous) nasal, or bronchial administration. Topical formulations are also included, for example, for topical antibiotic use.

It is noted that some of the compounds and isomers described herein thereof are also rather insoluble in water and, accordingly, liquid formulations which account for this factor may be made according to art-recognized pharmaceutical techniques. Examples of these techniques include an injection wherein the active compound is dissolved in a suitable solvent or co-solvent such as an appropriate polyethylene glycol, or a propylene glycol or the like; a sealed gelatin capsule enclosing an oily solution of the active compound; a suppository of the active compound in a conventional suppository base such as cocoa butter; or a liposome formulation, for example, the active compound and a glycerophospholipid such as phosphatidylcholine. In any event, the aforementioned characteristics of the subject compounds and isomers are not uncommon in the pharmaceutical art and, accordingly, art-recognized pharmaceutical techniques are employed to prepare appropriate formulations for such compounds, isomers or pharmaceutically acceptable salts of either.

The formulations may conveniently be presented in unit dosage form and may be prepared by any of the methods well known in the art of pharmacy. All methods include the step of bringing the active compound or salt into association with a carrier which constitutes one or more accessory ingredients. In general, the formulations are prepared by uniformly and intimately bringing the active compound or salt into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound (optionally in the form of a salt thereof); as a powder or granules; or in liquid form, e.g., as suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound (optionally in the form of a salt thereof) in, for example, a polyethylene glycol 200 or propylene glycol solution which is preferably isotonic with the blood of the recipient.

Useful formulations also comprise concentrated solutions or solids containing the active compound(s), any isomeric form thereof, or a pharmaceutically acceptable salt of the compound or isomeric form thereof, which upon dilution with an appropriate solvent give a solution suitable for parenteral administration.

Preparations for topical or local applications, which are, for example, conventional for preventing or treating bacterial infections of the skin, mouth, and eyes, comprise aerosol sprays, lotions, gels, ointments, etc. and pharmaceutically acceptable vehicles therefore such as, for example, lower aliphatic alcohols, polyglycerols such as glycerol, polyethyleneglycerol, esters of fatty acids, oils and fats, silicones, and other conventional topical carriers.

In topical formulations, the active compounds (or isomers thereof) are preferably utilized at concentrations of from about 0.1% to about 5.0% percent by weight.

In addition to the aforementioned ingredients, the formulations of this invention may further include one or more optional accessory ingredients(s) utilized in the art of pharmaceutical formulations, e.g., diluents, buffers, flavoring agents, binders, surface active agents, thickeners, lubricants, suspending agents, preservatives (including antioxidants) and the like.

The active compounds described herein (including all isomers) and salts thereof of the invention are intended to be administered under the guidance of a physician or veterinarian.

The amount of pharmacologically active compound (or any isomer thereof) or salt thereof required to be effective for antimicrobial treatment will, of course, vary with the individual mammal being treated and is ultimately at the discretion of the medical or veterinary practitioner. The factors to be considered include the condition being treated, the route of administration, the nature of the pharmaceutical composition, the mammal's body weight, surface area, age and general condition, and the particular compound or salt to be administered. In general, the pharmaceutical compositions of this invention contain from about 0.5 to about 500 mg and, preferably, from about 5 to about 350 mg of the active ingredient, preferably in a unit dosage form.

A suitable effective dose is in the range of about 0.1 to about 200 mg/kg body weight per day, preferably in the range of about 1 to about 100 mg/kg per day, calculated as the non-salt form of the active compound. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal (preferably a human), a dose range would be about 7.5 to about 1500 mg per day, and a typical dose would be about 800 mg per day. If discrete multiple doses are indicated, treatment might typically be 200 mg of a compound disclosed herein, given 4 times per day.

Topical Biocidal Compositions

The subject compounds are also useful for sterilizing surfaces and rendering them resistant to subsequent cellular growth. Thus, for example, one or more of the active ingredients disclosed herein, optionally in combination with a suitable carrier, can be used to treat the surfaces of implantable medical devices prior to their implantation. For instance, pacemakers, stents, shunts, catheters, and the like can be treated with the compounds of the subject invention to render these items free of cellular contamination in general and bacterial contamination in particular. Likewise, optical devices that are inserted into the body, such as endoscopes, bronchoscopes, and the like, can also be treated with compounds of the subject invention, thereby rendering the surface of the device microbe-free.

In practice, using the compounds of the present invention to treat a surface is a simple matter of contacting the surface with a sufficient amount of the active ingredient, for a time sufficient to allow the compound to exert its biocidal effect. The active ingredient can be applied neat, or in combination with a suitable carrier. Insofar as the active ingredients will not be injected or ingested into the body, the carrier for purposes of treating inanimate surfaces need not be pharmaceutically suitable.

Alternatively, the subject compounds can be covalently bonded to the surface of interest. In one approach, the fully-formed compounds can be attached covalently using the same chemistries described herein. Also, the subject compounds can be synthesized directly attached to the surface via covalent bonds by polymerizing the compounds de novo from an initiator group that is covalently attached to the surface of interest. Again, this can be accomplished using the chemistries described herein.

EXAMPLES

The following Examples are included solely to provide a more clear and consistent understanding of the invention disclosed and claimed herein.

Materials: Substituted styrenes (liquid) (obtained commercially from Monomer-Polymer/Dajac Laboratories. Feasterville, Pa.) were purified by vacuum distillation (representative boiling points: DMAS 1, 73° C. at 1.7 mm Hg; 2, 122-125° C. at 1.8 mm Hg; 3, 42° C. at 0.75 mm Hg) and stored at −80° C. until use. Styrene 4 (Aldrich, Milwaukee, Wis.) was purified by passage through an inhibitor-removal column (SDTR-7, Scientific Polymer Products, Ontario, N.Y.) immediately before use. VBC (a 68:32 mixture of m- and p-isomers, Aldrich) was purified by vacuum distillation immediately before use. Benzene was distilled from sodium benzophenone ketyl. Methanol was distilled from Mg (OMe)$_2$. AIBN, dodecyldimethylamine, and (ar-vinylbenzyl) trimethylammonium chloride 5 (Aldrich) were used without further purification. Monomer 6 was synthesized from VBC and dodecyldimethylamine by the procedure of Ikeda et al.[16]

General Procedure for Polymerizations and Stock Solutions: Monomer (2.00 mmol total) was degassed by three freeze-pump-thaw cycles in a 25 mL Schlenck flask. AIBN was flushed with $N_2$ for 1 h and dissolved to 16.4 mg/mL (0.1 M) in degassed benzene. A 1 mL aliquot of this solution was added to the Schlenck flask, which was heated to 60° C. with stirring for 2 d. The reaction mixture was concentrated under centrifugation, resuspended in chloroform, applied to a column of Sephadex LH-20 (20 mm diameter×75 mm length), eluted with chloroform, and collected as an 8 mL pre-run, 1-2 mL fractions, and a post-run. RP-TLC (Whatman LKC 18F plates, MeOH eluent, UV visualization) was used to check fractions for residual monomer ($R_f$~0.5). Fractions showing only the baseline polymer streak were pooled and concentrated under centrifugation. This procedure afforded each purified polymer as a clear oil.

Chloride salts of polymers were obtained by dissolving the polymers, in vials, in 0.02 N HCl (prepared by dilution of sterile-filtered 1.0 N HCl (Sigma, St. Louis, Mo.) with Millipore water) to a concentration of 2 mg/mL, then drying by centrifugal evaporation with heating to 80° C. for 5-10 h. Millipore water was then added to the vials to give stock solutions (2 mg/mL) of free-amine polymer (not accounting for the added weight due to formation of the HCl salt). Poly (5) was directly soluble in water. Poly(6) was first dissolved in 2:1 (v/v) DMF:ethanol to a concentration of 33 mg/mL, in accordance with Senuma et al.[18,19] and then diluted with Millipore water to stock concentration of 2 mg/mL. This solution was allowed to stand overnight at room temperature; no precipitation was observed. Solute-free DMF:ethanol was similarly diluted to serve as an organic solvent blank. These stock solutions were used in the Orange OT solubilization, ANS binding, antibacterial activity, and hemolysis assays described herein.

Characterization Data for Polymers: The following polymers were synthesized and purified as described above, and then characterized by various methods, including percent yield, elemental analysis, $^1$H and $^{13}$C NMR, gel permeation chromatography (GPC, also known as size-exclusion chromatography), UV-Vis spectroscopy, and mass spectrometry. The results were as follows:

Poly(1): 17.7 mg (110 μmol, 5.5%). $^1$H NMR δ (CDCl$_3$, 300 MHz) 0.887 ppm (lump, 0.17H), 1.066 ppm (lump, 0.14H), 1.362 ppm (lump, 1.79H, backbone), 1.673 ppm (lump, 1.11H, backbone), 2.154 ppm (double lump, 6.08H, Me$_2$N), 2.677 ppm (lump, 0.36H), 3.266 ppm (br lump, 1.94H, ArCH$_2$N), 6.385 ppm (lump, 1.84H, aromatic), 6.91 ppm (lump, 2.12H, aromatic). $^{13}$C NMR δ (CDCl$_3$, 75 MHz) 45.247 ppm (negative to DEPT-135, NMe$_2$). UV/Vis (MeOH) 204 nm (ϵ=589200 cm$^2$/g), 258 nm (ϵ=44800 cm$^2$/g). GPC $M_w$=8.14 KDa, $M_n$=2.49 KDa, PDI=3.27.

Poly(1:2)3: 64.5 mg (396 μmol, 20%). $^1$H NMR δ (CDCl$_3$, 300 Mhz) 0.9 ppm (lump, 0.27H, octyl methyl), 1.051 ppm (lump, 0.16H), 1.296 ppm (lump, 2.16H, backbone, octyl), 1.652 ppm (lump, 1.18H, backbone), 2.152 ppm (double lump, 6.47H, Me$_2$N), 2.441 ppm (lump, 0.07H. ArCH$_2$ octyl), 3.242 ppm (br lump, 1.91H, ArCH$_2$N), 6.393 ppm (lump, 1.82H, aromatic), 6.909 ppm (lump, 2.14H, aromatic). GPC $M_w$=8.57 KDa, $M_n$=3.29 KDa, PDI=2.60.

Poly(1:2)5: 33.2 mg (202 μmol, 10%). $^1$H NMR δ (CDCl$_3$, 300 MHz) 0.896 ppm (irregular lump, 0.33H, octyl methyl), 1.063 ppm (lump, 0.15H), 1.296 ppm (lump, 2.37H, backbone, octyl), 1.587 ppm (lump, 1H, backbone), 2.08 ppm (two lumps, 5.78H, Me$_2$N), 2.444 ppm (lump, 0.19H, octyl ArCH$_2$), 3.291 ppm (br lump, 1.83H, ArCH$_2$N), 4.603 ppm (lump, 0.06H), 6.372 ppm (lump, 1.82H, aromatic), 6.883 ppm (lump, 2.18H, aromatic). GPC $M_w$=9.87 KDa, $M_n$=2.21 KDa, PDI=4.47.

Poly(1:2)7: 44.2 mg (268 μmol, 13%). $^1$H NMR δ (CDCl$_3$, 300 Mhz) 0.896 ppm (lump, 0.45H, octyl methyl), 1.068 ppm (lump, 0.22H), 1.264 ppm (lump, 2.38H, backbone, octyl), 1.763 ppm (lump, 2.82H, backbone), 2.164 ppm (double lump, 5.95H, Me$_2$N), 2.454 ppm (lump, 0.16H, ArCH$_2$ octyl), 3.233 ppm (br lump, 1.89H, ArCH$_2$N), 6.386 ppm (lump, 1.7H, aromatic), 6.887 ppm (lump, 2.23H, aromatic). UV/Vis (MeOH) 204 nm (ϵ=284900 cm$^2$/g), 256 nm (ϵ=23000 cm$^2$/g). GPC $M_w$=11.0 KDa, $M_n$=2.94 KDa, PDI=3.75.

Poly(1:2)10: 37.3 mg (224 µmol, 11%). $^1$H NMR δ (CDCl$_3$, 300 MHz) 0.882 ppm (lump, 0.57H, octyl methyl), 1.294 ppm (lump, 2.88H, octyl, backbone), 1.657 ppm (multiple lumps, 2.63H, backbone, water), 2.139 ppm (two lumps, 5.87H, Me$_2$N), 2.475 ppm (lump, 0.27H, ArCH$_2$ octyl), 3.214 ppm (two lumps, 2.05H, ArCH$_2$N), 6.407 ppm (lump, 1.63H, aromatic), 6.909 ppm (lump, 2.36H, aromatic). $^{13}$C NMR δ (CDCl$_3$, 75 MHz) 44.923 ppm (NMe$_2$). UV/Vis (MeOH) 204 nm (ϵ=361100 cm$^2$/g), 268 nm (ϵ=28500 cm$^2$/g). GPC M$_w$=10.3 KDa, M$_n$=3.44 KDa, PDI=3.00.

Poly(1:2)15: 57.1. mg (337 µmol, 17%). $^1$H NMR δ (CDCl$_3$, 300 MHz) 0.898 ppm (lump, 0.86H, octyl methyl), 1.302 ppm (multiple lumps, 5.04H, backbone, octyl), 2.15 1 ppm (two lumps, 4.7H, Me$_2$N), 2.405 ppm (lump, 1.44H, ArCH$_2$octyl), 3.231 ppm (lump, 1.99H, ArCH$_2$N), 6.408 ppm (lump, 1.77H, aromatic), 6.924 ppm (lump, 2.15H, aromatic). GPC M$_w$=5.74 KDa, M$_n$=2.85 KDa, PDI=2.01.

Poly(1:2)20: 26.9 mg (156 µmol, 7.8%). $^1$H NMR δ (CDCl$_3$, 300 MHz) 0.896 ppm (lump, 0.83H, octyl methyl), 1.295 ppm (lump, 3.72H, octyl, backbone), 1.673 ppm (multiple lumps, 2.26H, backbone, water), 2.148 ppm (two lumps, 4.99H, Me$_2$N), 2.486 ppm (lump, 0.46H, ArCH$_2$ octyl), 3.207 ppm (two lumps, 1.67H, ArCH$_2$N), 6.407 ppm (lump, 1.75H, aromatic), 6.932 ppm (lump, 2.23H, aromatic).

Poly(1:2)30: 7.40 mg (41.6 µmol, 2.1%). $^1$H NMR δ (CDCl$_3$, 300 MHz) 0.895 ppm (lump, 1.37H, octyl methyl), 1.298 ppm (multiple lumps, 6.96H, backbone, octyl), 2.164 ppm (two lumps, 4.39H, Me$_2$N), 2.466 ppm (lump, 1.96H, ArCH$_2$ octyl), 3.303 ppm (two lumps, 2.06H, ArCH$_2$N), 6.396 ppm (lump, 1.69H, aromatic), 6.93 ppm (lump, 2.25H, aromatic). GPC M$_w$=5.82 KDa, M$_n$=3.01 KDa, PDI=1.94.

Poly(1:2)35: 13.3 mg (73.7 µmol, 3.7%). $^1$H NMR δ (CDCl$_3$, 300 MHz) 0.895 ppm (lump, 1.29H, octyl methyl), 1.293 ppm (lump, 5.26H, octyl, backbone), 1.695 ppm (multiple lumps, 1.44H, backbone, water), 2.15 ppm (two lumps, 4.02H, Me$_2$N), 2.479 ppm (lump, 0.78H, ArCH$_2$ octyl), 3.225 ppm (two lumps, 1.18H, ArCH$_2$N), 6.41 ppm (lump, 1.8H, aromatic), 6.909 ppm (lump, 2.17H, aromatic).

Poly(1:3)3: 71.6 mg (445 µmol, 22%). $^{13}$C NMR δ (CDCl$_3$, 75 MHz) 126.256 ppm (broad, positive to DEPT-135, aromatic), 127.15 ppm (broad, positive to DEPT-135, aromatic), 127.815 ppm (broad, positive to DEPT-135, aromatic), 128.535 ppm (broad, positive to DEPT-135, aromatic), 40.281 ppm (positive to DEPT-135, backbone), 45.202 ppm (positive to DEPT-135, NMe$_2$), 64.056 ppm (negative to DEPT135, ArCH$_2$N), 64.249 ppm (negative to DEPT-135, ArCH$_2$N). $^1$H NMR δ (CDCl$_3$, 300 MHz) 0.886 ppm (lump, 0.16H, backbone), 1.061 ppm (lump, 0.21H, backbone), 1.363 ppm (lump, 1.92H, backbone, iPr), 1.727 ppm (lump, 0.97H, backbone), 2.141 ppm (two lumps, 5.89H, NMe$_2$), 3.285 ppm (double lump, 1.95H, ArCH$_2$N), 6.413 ppm (lump, 1.75H, aromatic), 6.912 ppm (lump, 2.13H, aromatic). GPC M$_w$=7.55 KDa, M$_n$=2.56 KDa, PDI=2.95.

Poly(1:3)5: 22.6 mg (141 µmol, 7.0%). $^1$H NMR δ (CDCl$_3$, 300 MHz) 0.888 ppm (lump, 0.19H, backbone), 1.335 ppm (lump, 2.22H, backbone, iPr), 1.664 ppm (lump, 0.97H, backbone), 2.146 ppm (two lumps, 5.94H, NMe$_2$), 2.829 ppm (lump, 0.26H, iPr ArCH$_2$), 3.229 ppm (double lump, 1.82H, ArCH$_2$N), 6.382 ppm (lump, 1.85H, aromatic), 6.913 ppm (lump, 2.14H, aromatic). $^{13}$C NMR δ (CDCl$_3$, 75 MHz) 127.621 ppm (lump, positive to DEPT-135, aromatic), 45.227 ppm (positive to DEPT-135, NMe$_2$), 64.268 ppm (lump, negative to DEPT-135, ArCH$_2$N). GPC M$_w$=8.63 KDa, M$_n$=3.35 KDa, PDI=2.58.

Poly(1:3)7: 28.3 mg (177 µmol, 8.8%). $^1$H NMR δ (CDCl$_3$, 300 Mhz) 0.891 ppm (lump, 0.1H, backbone), 1.059 ppm (lump, 0.22H, backbone), 1.361 ppm (lump, 2.22H, backbone, iPr), 1.684 ppm (lump, 0.88H, backbone), 2.143 ppm (two lumps, 5.98H, NMe$_2$), 3.217 ppm (double lump, 1.86H, ArCH$_2$N), 6.391 ppm (lump, 1.85H, aromatic), 6.913 ppm (lump, 2.18H, aromatic). $^{13}$C NMR δ (CDCl$_3$, 75 MHz) 126.384 ppm (positive to DEPT-135, aromatic), 127.226 ppm (positive to DEPT-135, aromatic), 127.362 ppm (positive to DEPT-135, aromatic), 127.803 ppm (positive to DEPT-135, aromatic), 128.484 ppm (positive to DEPT-135, aromatic), 128.571 ppm (positive to DEPT-135, aromatic), 40.236 ppm (positive to DEPT-135, iPr methyls), 45.241 ppm (positive to DEPT-135, NMe$_2$), 64.085 ppm (negative to DEPT-135, ArCH$_2$N), 64.302 ppm (negative to DEPT-135, ArCH$_2$N). IR (thin film) 1032 cm$^{-1}$ (s), 1100 cm$^{-1}$ (w), 1148 cm$^{-1}$ (w), 1178 cm$^{-1}$ (m), 1264 cm$^{-1}$ (m), 1368 cm$^{-1}$ (m), 1458 cm$^{-1}$ (s), 2770 cm$^{-1}$ (s), 2812 cm$^{-1}$ (s), 2856 cm$^{-1}$ (w), 2932 cm$^{-1}$ (s), 712 cm$^{-1}$ (s), 794 cm$^{-1}$ (m), 816 cm$^{-1}$ (w), 846 cm$^{-1}$ (m), 860 cm$^{-1}$ (m), 898 cm$^{-1}$ (w), 988 cm$^{-1}$ (w). UV-Vis (MeOH) 204 nm (ϵ=418400 cm$^2$/g), 258 nm (ϵ=30200 cm$^2$/g). GPC M$_w$=7.45 KDa, M$_n$=2.86 KDa, PDI=2.61.

Poly(1:3)10: 17.3 mg (108 µmol, 5.4%). $^1$H NMR δ (CDCl$_3$, 300 MHz) 0.817 ppm (lump, 0.2H, backbone), 1.284 ppm (lump, 2.61H, backbone, iPr), 1.669 ppm (lump, 0.97H, backbone), 2.153 ppm (two lumps, 5.78H, NMe$_2$), 2.78 1 ppm (lump, 0.18H, iPr ArCH$_2$), 3.239 ppm (double lump, 1.7 1H, ArCH$_2$N), 6.404 ppm (lump, 1.86H, aromatic), 6.911 ppm (lump, 2.14H, aromatic). $^{13}$C NMR δ (CDCl$_3$, 75 MHz) 127.869 ppm (lump, positive to DEPT-135, aromatic), 45.178 ppm (positive to DEPT-135, NMe$_2$), 64.122 ppm (lump, negative to DEPT-135, ArCH$_2$N). GPC M$_w$=9.16 KDa, M$_n$=2.71 KDa, PDI=3.38.

Poly(1:3)15: 31.8 mg (200 µmol, 10%). $^1$H NMR δ (CDCl$_3$, 300 MHz) 0.894 ppm (lump, 0.14H, backbone), 1.08 1 ppm (lump, 0.3 1H, backbone), 1.361 ppm (lump, 2.57H, backbone, iPr), 1.684 ppm (lump, 0.93H, backbone), 2.145 ppm (two lumps, 5.13H, NMe$_2$), 3.219 ppm (double lump, 1.69H. ArCH$_2$N), 6.406 ppm (lump, 1.78H, aromatic), 6.916 ppm (lump, 2.11H, aromatic). $^{13}$C NMR δ (CDCl$_3$, 75 MHz) 126.402 ppm (broad, positive to DEPT-135, aromatic), 127.304 ppm (broad, positive to DEPT-135, aromatic), 127.863 ppm (broad, positive to DEPT-135, aromatic), 128.62 ppm (broad, positive to DEPT-135, aromatic), 40.237 ppm (positive to DEPT-135, backbone), 45.217 ppm (positive to DEPT-135, NMe$_2$), 64.094 ppm (negative to DEPT-135, ArCH$_2$N), 64.319 ppm (negative to DEPT135, ArCH$_2$N). GPC M$_w$=10.3 KDa, M$_n$=3.32 KDa, PDI=3.09.

Poly(1:3)20: 24.4 mg (154 µmol, 7.7%). $^1$H NMR δ (CDCl$_3$, 300 Mhz) 0.86 ppm (lump, 0.18H, backbone), 1.186 ppm (lump, 3.16H, backbone, iPr), 1.706 ppm (lump, 0.93H, backbone), 2.153 ppm (two lumps, 5.06H, NMe$_2$), 2.767 ppm (lump, 0.17H, iPr ArCH$_2$), 3.239 ppm (double lump, 1.66H, ArCH$_2$N), 6.404 ppm (lump, 1.84H, aromatic), 6.911 ppm (lump, 2.17H, aromatic). $^{13}$C NMR δ (CDCl$_3$, 75 Mhz) 127.23 ppm (lump, positive to DEPT-135, aromatic), 24.038 ppm (positive to DEPT-135, isopropyl), 40.196 ppm (lump, positive to DF.PT-135, isopropyl), 45.19 ppm (positive to DEPT-135, NMe$_2$), 64.051. ppm (negative to DEPT-135, ArCIHN$_2$), 64.272 ppm (negative to DEPT-135, ArCHN$_2$). GPC M$_w$=9.50 KDa, M$_n$=3.26 KDa, PDI=2.91.

Poly(1:3)30: 104 mg (663 µmol, 33%). $^1$H NMR δ (CDCl$_3$, 300 MHz) 0.896 ppm (lump, 0.22H, backbone), 1.186 ppm (overlapping lumps, 3.73H, backbone, isopropyl), 1.732 ppm (lump, 2H, backbone), 2.158 ppm (two lumps, 4.28H, Me$_2$N), 2.796 ppm (lump, 0.32H), 3.253 ppm (double lump, 1.39H, ArCH$_2$N), 6.47 ppm (lump, 1.76H, aromatic), 6.92 ppm (lump, 2.24H, aromatic). GPC M$_w$=7.63 KDa, M$_n$=3.07 KDa, PDI=2.49.

Poly(1:4)3: 62.2 mg (390 µmol, 19%). $^1$H NMR δ (CDCl$_3$, 300 MHz) 0.895 ppm (lump, 0.18H, backbone), 1.336 ppm (lump, 1.96H, backbone), 1.719 ppm (lump, 2.29H, backbone), 2.145 ppm (two lumps, 5.84H, Me$_2$N), 3.246 ppm (lump, 1.94H, ArCH$_2$N), 6.377 ppm (lump, 1.77H, aromatic), 6.899 ppm (lump, 2.24H, aromatic). GPC $M_w$=8.19 KDa, $M_n$=3.22 KDa, PDI=2.54.

Poly(1:4)5: 79.2 mg (500 µmol, 25%). $^1$H NMR δ (CDCl$_3$, 300 MHz) 0.888 ppm (lump, 0.2H, backbone), 1.065 ppm (lump, 0.21H, backbone), 1.363 ppm (lump, 2.07H, backbone), 1.664 ppm (lump, 1.14H, backbone), 2.143 ppm (two lumps, 6.68H, NMe$_2$), 3.219 ppm (double lump, 2H, ArCH$_2$N), 6.382 ppm (lump, 2.13H, aromatic), 6.924 ppm (lump, 2.52H, aromatic). $^{13}$C NMR δ (CDCl$_3$, 75 MHz) 126.344 ppm (broad, positive to DEPT-135, aromatic), 127.096 ppm (broad, positive to DEPT-135, aromatic), 127.816 ppm (broad, positive to DEPT-135, aromatic), 128.522 ppm (broad, positive to DEPT-135, aromatic), 40.189 ppm (positive to DEPT-135, backbone), 45.183 ppm (positive to DEPT-135, NMe$_2$), 63.991 ppm (negative to DEPT-135, ArCH$_2$N), 64.232 ppm (negative to DEPT-135, ArCH$_2$N). GPC $M_w$=8.17 KDa, $M_n$=3.12 KDa, PDI=2.62.

Poly(1:4)7: 15.6 mg (99.2 µmol, 5.0%). $^1$H NMR δ (CDCl$_3$, 300 Mhz) 0.895 ppm (lump, 0.18H, backbone), 1.32 ppm (lump, 1.91H, backbone), 1.826 ppm (lump, 1.6H, backbone), 2.145 ppm (two lumps, 5.71H, Me$_2$N), 3.27 ppm (lump, 1.85H, ArCH$_2$N), 6.326 ppm (lump, 1.75H, aromatic), 6.865 ppm (lump, 2.25H, aromatic). $^{13}$C NMR δ (CDCl$_3$, 75 MHz) 127.344 ppm (multiple positive peaks on DEPT-135, aromatic), 45.285 ppm (positive to DEPT-135, NMe$_2$), 64.384 ppm (lumpy, negative to DEPT-135, ArCH$_2$N). UV/Vis (MeOH) 204 nm (ε=468000 cm$^2$/g), 256 nm (ε=26300 cm$^2$/g). GPC $M_w$=4.56 KDa, $M_n$=1.85 KDa, PDI=2.47.

Poly(1:4)10: 44.0 mg (283 µmol, 14%). $^1$H NMR δ (CDCl$_3$, 300 MHz) 0.896 ppm (lump, 0.21H, backbone), 1.076 ppm (lump, 0.2H, backbone), 1.375 ppm (lump, 1.88H, backbone), 1.689 ppm (lump, 1.09H, backbone), 2.153 ppm (two lumps, 5.89H, NMe$_2$), 3.226 ppm (double lump, 2H, ArCH$_2$N), 6.408 ppm (lump, 1.85H, aromatic), 6.946 ppm (lump, 2.46H, aromatic). $^{13}$C NMR δ (CDCl$_3$, 75 Mhz) 127.83 ppm (broad, positive to DEPT-135, aromatic), 40.325 ppm (positive to DEPT-135, backbone), 45.227 ppm (positive to DEPT-135, NMe$_2$), 64.015 ppm (negative to DEPT-135, ArCH$_2$N), 64.275 ppm (negative to DEPT-135, ArCH$_2$N). GPC $M_w$=8.19 KDa, $M_n$=3.17 KDa, PDI=2.58.

Poly(1:4)15: 18.4 mg (121 µmol, 6.0%). $^1$H NMR δ (CDCl$_3$, 300 MHz) 0.897 ppm (lump, 0.13H, backbone), 1.276 ppm (lump, 2.06H, backbone), 1.673 ppm (lump, 3.36H, backbone), 2.157 ppm (two lumps, 5.1 H, Me$_2$N), 3.27 ppm (lump, 1.82H, ArCH$_2$N), 6.377 ppm (lump, 1.7H, aromatic), 6.938 ppm (lump, 2.32H, aromatic). GPC $M_w$=9.82 KDa, $M_n$=3.21 KDa, PDI=3.06.

Poly(1:4)20: 54.6 mg (364 µmol, 18%). $^1$H NMR δ (CDCl$_3$, 300 MHz) 0.884 ppm (lump, 0.18H, backbone), 1.072 ppm (lump, 0.19H, backbone), 1.369 ppm (lump, 2.1H, backbone), 1.7 ppm (lump, 1.19H, backbone), 2.149 ppm (two lumps, 6.11H, NMe$_2$), 3.281 ppm (double lump, 2H, ArCH$_2$N), 6.411 ppm (lump, 2.15H, aromatic), 6.951 ppm (lump, 2.87H, aromatic). $^{13}$C NMR δ (CDCl$_3$, 75 MHz) 126.402 ppm (broad, positive to DEPT-135, aromatic), 127.304 ppm (broad, positive to DEPT-135, aromatic), 127.863 ppm (broad, positive to DEPT-135, aromatic), 128.62 ppm (broad, positive to DEPT-135, aromatic), 40.237 ppm (positive to DEPT-135, backbone), 45.217 ppm (positive to DEPT-135, NMe$_2$), 64.094 ppm (negative to DEPT-135, ArCH$_2$N), 64.3 19 ppm (negative to DEPT-135, ArCH$_2$N). GPC $M_w$=8.84 KDa, $M_n$=3.41 KDa, PDI=2.59.

Poly(1:4)30: 36.8 mg (255 µmol, 13%). $^1$H NMR δ (CDCl$_3$, 300 MHz) 0.905 ppm (lump, 0.1H, backbone), 1.369 ppm (lump, 1.86H, backbone), 1.728 ppm (lump, 1.8H, backbone), 2.153 ppm (two lumps, 4.05H, Me$_2$N), 3.225 ppm (lump, 1.32H, ArCH$_2$N), 6.434 ppm (lump, 1.69H, aromatic), 6.955 ppm (lump, 2.31H, aromatic). GPC $M_w$=11.1 KDa, $M_n$=4.96 KDa, PDI=2.24.

TLC Assay for Copolymerization: A representative Sephadex-purified sample from each polymer series (poly(1:2)3, poly(1:3)7. and poly(1:4)30) was spotted on Whatman K6F silica gel (60 Å particle size). As controls, pure poly(1) and polystyrene molecular weight standards (4 KDa and a standard mixture with $M_p$=2,930 Da, 28.5 KDa, 148 KDa, 842 KDa, and 7.50 MDa) were spotted onto the same plate. The plate was eluted with 1% (v/v) glacial acetic acid/ethyl acetate and visualized by UV. Poly(1) eluted as a streak with $R_f$<0.3; polystyrene standards eluted near the solvent front ($R_f$>0.9 for the 4 KDa sample, Rf>0.7 for the standard mixture). All three experimental samples showed TLC patterns identical to poly(1), with no UV activity at Rf>0.3.

Determination of Apparent Molecular Weight: GPC was carried out at ambient temperature (23-25° C.) using a Shimadzu HPLC system and pair (in series) of 300×7.5 mm PLgel Mixed D columns (5 p.m pore size, Polymer Laboratories, Amherst, Mass.). Calibration was performed using polystyrene standards (EasiCal PS-1, Polymer Laboratories) of $M_p$ 841.7, 320, 148, 59.5, 28.5, 10.85, 2.93, and 0.58 KDa. Polymers were dissolved in eluent (0.1% TEA, freshly distilled from CaH$_2$, in HPLC-grade THF, Aldrich) to concentrations of ~5 mg/mL, and 30 µL injections were made. Ultraviolet absorbance data was collected using Shimadzu CLASS-VP software (version 7.1.1) and exported to Microsoft Excel. A baseline was determined by linear regression analysis of peak-free regions and subtracted from the trace. The baseline-corrected trace was then, integrated according to the method described by Yau et al.[30] to determine $M_w$ and $M_n$. Correction for peak spreading was not performed. PDI was calculated as $M_w/M_n$.

Separate GPC analysis, performed on a representative subset of samples using a variety of PLgel columns using ELS detection, showed similar apparent MW. However, GPC performed on a Waters instrument in 2% NMP/THF, using a pair of Waters Styragel HT6E columns and RI detection, gave consistently larger apparent MW values (by approximately a factor of 3). This may be due to the 5 KDa lower detection limit of the Styragel columns and is mentioned as a caution that GPC-determined molecular weights are apparent.

Partial Fractionation: Samples of poly(1) and copoly($1_{97}$:$2_3$), ($1_{95}$:$2_5$), ($1_{93}$:$2_7$), ($1_{90}$:$2_{10}$), ($1_{85}$:$2_{15}$), ($1_{80}$:$2_{20}$), and ($1_{70}$:$2_{30}$), were dissolved in 0.2N HCl (prepared by dilution of sterile-filtered 1.0N HCl with Millipore water) to a concentration of 1-2 mg/mL One to ten mL (1-10 mL) of these solutions were added to Amicon Centriplus YM-50 filter units (Millipore, Bedford, Mass.), which had been rinsed once with Millipore water. The filter units were centrifuged at 3000×g for 30 min. The retentates were collected by inverted spin retrieval. The filtrates were then transferred to YM-30 filter units and centrifuged for 30 min. Further serial filtration through YM-10 (90 min) and YM-3 (250 min) filter units gave five fractions (i.e., the fractions retained by YM-50, retained by YM-30, retained by YM-10, retained by YM-3, and filtrate), which were dried by centrifugal evaporation. GPC analysis was performed as described above.

Dye Solubilization: Orange OT (Aldrich) was dissolved in ACS reagent-grade acetone, precipitated with Millipore water, recrystallized twice from absolute EtOH, and dried overnight under vacuum. Stock solutions of polymers (2 mg/ml), prepared as described above, were diluted with Millipore water to give total volumes of 500 µL at the concentration to be examined; mock dilutions of Millipore water were performed simultaneously to provide a separate blank for each polymer concentration. Two identical vials of each polymer sample at each concentration were prepared; a small amount of Orange OT (less than would cover the tip of a small spatula) was added to one, and the other (treated identically but containing no Orange OT) was used as a spectroscopic blank to correct for absorbance of the polymer. All vials were agitated gently for 3 d at room temperature on a blood-rocker and then filtered through cotton to remove undissolved orange OT. An aliquot (200 µL) of each sample was diluted with 800 µL of absolute EtOH, and absorbance of each solution was measured (1.0 cm path length cell, HP 8452 UV/visible spectrometer) at 500 nm (Orange OT absorbance) and 340 nm (background, to correct for baseline drift). Net absorbance ($OD_{500}$-$OD_{340}$), using the Orange OT-free samples as spectroscopic blanks and corrected for net absorbance of the polymer-free samples, was determined.

ANS Fluorescence: A 10 mM stock solution of high-purity ANS (Molecular Probes, Eugene Oreg.) was prepared in Millipore water and transferred to a foil-wrapped vial. Vials were charged with 382.5 µL of 50 mM freshly prepared Tris buffer (pH 6.8 at 23° C. in Millipore water, to avoid the pH dependence of ANS fluorescence, which arises below pH 6.0); 7.5 µL of polymer stock solutions (2 mg/mL), prepared as described above, or Millipore water (as a polymer-free blank) were added to pairs of vials. Ten µL of ANS stock solution was then added to one (1) vial from each pair, and 10.0 µL of Millipore water to the other, to give 400 µL of solutions that were ~250 µM in monomer residue and either 0 µM (ANS-free blank) or 250 µM in ANS.

Fluorescence spectra were measured in a single session on a Hitachi F-4500 fluorescence spectrophotometer. Excitation and emission slit widths were set to 5 nm. Samples were excited at 350 nm; emission spectra were collected from 370 nm to 650 nm. Polymer fluorescence in the ANS-free blanks was of negligible intensity compared to the fluorescence of the ANS-containing samples, but the corresponding ANS-free blank spectrum was subtracted from each ANS-containing sample spectrum.

Biological Properties:

MIC, MBC, and hemolysis assays were performed based upon a standard protocols, as described herein Minimal Inhibitory Concentration (MIC): Stock solutions of polymers (5.00 µL at 2 mg/mL, prepared as described above), commercial synthetic ($Ala^{8,3,18}$)-1-magainin-2-amide (Sigma, dissolved in Millipore water to 1 mg/mL, 10.0 µL, as positive control), or solvent blank (5.00 µL) were diluted into brain-heart infusion (BHI) broth in row A of 96-well sterile assay plates (B-D Falcon 35-3075, Fisher Scientific) and seven serial twofold dilutions were performed to give 50 µL of peptide solution (at double the final assay concentration) in each well. Bacterial strains (*Escherichia coli* JM109, *Bacillus subtilis* BR151,[24] *Staphylococcus aureus* 5332 (a clinical MRSA isolate from the Weisblum laboratory strain collection), and *Enterococcus faecium* A436[25]) were grown on 2% bacteriological agar in BHI medium. Cells from these cultures were suspended in BHI broth at a concentration of approximately $10^6$ colony-forming units (CFU)/mL, and 50 µL of cell suspension was added to each well to give a total of 100 µL in each well.

Plates were then incubated at 37° C. for 6 h. Bacterial growth gives rise to turbidity and light scattering, which was detected by measuring $OD_{650}$ using a Molecular Devices Emax microplate reader connected to a Windows computer running SOFTmax v.2.34. $OD_{650}$ values from two simultaneous experiments were averaged. MIC, the concentration at which growth is completely inhibited, is reported as the median value of at least three experiments from separately diluted bacterial suspensions, at least two of which were performed on different days. If an even number of experiments was performed and the two median values were not identical, the geometric mean is reported as the MIC.

Minimal Bactericidal Concentration (MBC): To determine cell viability, 10 µL from each of the MIC, 2×MIC, and 4×MIC wells (up to the maximum concentration of 50 µL/mL) was diluted 100-fold. Of this, 100 µL (containing at most $5 \times 10^2$ CFU) was plated on 2% bacteriological agar in BHI medium and incubated at 37° C. overnight (for *B. subtilis*) or for 4 d (for *E. coli*, because no growth was seen after 10 h; colonies appeared on some plates after extended incubation). The absence of colonies was considered indicative of >99% bacterial killing, and the lowest assay well concentration showing no colonies is reported as the MBC.

Hemolysis Assay: Sterile TBS (Tris buffered saline: 10 mM Tris, 150 mM NaCl, pH 7.2) was prepared and used to dilute stock solutions of polymers (5.00 µL at 2 mg/mL prepared as described above), commercial synthetic melittin (Sigma, dissolved in Millipore water to 1 mg/mL, 10.0 µL, as positive control), or solvent blank (5.00 µL) in row A of 96-well sterile assay plates. Seven serial twofold dilutions were performed to give 20 µL of peptide solution (at five times the final assay concentration) in each well. Freshly drawn human red blood cells (hRBC, blood type A, collected into a Becton-Dickinson EDTA-anticoagulant vacuum container, refrigerated, and used within 8 h) were washed with TBS three times or until the supernatant was clear, then suspended in TBS at 1% (v/v). Eighty (80) µL of hRBC suspension was added to each well, giving a total assay volume of 100 µL. Plates were then incubated at 37° C. for 1 h and centrifuged at 3500 rpm for 5 mm to pellet intact hRBC. Supernatant (80 µL) was diluted with 80 µL of twice-distilled water and hemoglobin concentration measured (as $OD_{450}$) with a Molecular Devices Emax microplate reader. At this point, absorbance values were averaged across two identical plates. The most concentrated melittin well in the plate (200 µL/mL or 50 µL/mL) was used as a reference for 100% hemolysis; water blank was used as a reference for 0% hemolysis, and percent hemolysis was calculated as $\{OD_{450}(sample) - OD_{450}(buffer)\} / \{OD_{450}(melittin) - OD_{450}(buffer)\}$. The mean hemolysis percentage for a given polymer at a given concentration was calculated, based on at least two separate experiments performed on different days (except for poly(6), where two experiments were performed simultaneously).

The results are presented in Tables 2 and 3:

TABLE 2

Biological Results for Various Polymers and Co-Polymers Againts *E. Coli* and *B. Subtilis*: MBC

| Strain | *E. coli* JM109 | | | *B. subtilis* BR151 | | |
|---|---|---|---|---|---|---|
| Comonomer | 2 | 3 | 4 | 2 | 3 | 4 |
| 0% [poly(1)] | 50 | | | 50 | | |
| 3% | >50 | >50 | >50 | 12.5 | 25 | 50 |
| 5% | 50 | —a | — | 25 | 50 | 12.5 |
| 7% | >50 | 50 | >50 | 25 | 50 | 25 |
| 10% | 50 | — | — | 25 | 25 | 25 |

TABLE 2-continued

Biological Results for Various Polymers and Co-Polymers Againts *E. Coli* and *B. Subtilis*: MBC

| Strain | E. coli JM109 | | | B. subtilis BR151 | | |
|---|---|---|---|---|---|---|
| Comonomer | 2 | 3 | 4 | 2 | 3 | 4 |
| 15% | — | — | — | 25 | 25 | 25 |
| 20% | — | — | — | >50 | 25 | 12.5 |
| 30% | — | — | — | >50 | 25 | 50 |
| 35% | — | — | — | >50 | — | — |
| (Ala8,13,18)-magainin 2 amide | 25 | | | — | | | aNot determined.

TABLE 3

Biological Results for Various Polymers and Co-Polymers Againts *E. Coli*, *B. Subtilis*, *S. aureus*, and *E Faecium*: MIC

| Strain | E. coli JM109 | | | B. subtilis BR151 | | | S. aureus 5332 | | | E. faecium A436 | | |
|---|---|---|---|---|---|---|---|---|---|---|---|---|
| Comonomer | 2 | 3 | 4 | 2 | 3 | 4 | 2 | 3 | 4 | 2 | 3 | 4 |
| 0% [poly(1)] | 25 | | | 12.5 | | | 50 | | | 12.5 | | |
| 3% | 50 | 25 | 25 | 12.5 | 6.3 | 8.87 | 25 | 25 | 50 | 6.3 | 6.3 | 12.5 |
| 5% | 50 | 25 | 50 | 12.5 | 8.87 | 35.4 | 25 | 25 | >50 | 6.3 | 6.3 | 25 |
| 7% | 25 | 25 | 25 | 6.3 | 6.3 | 8.87 | 12.5 | 50 | 50 | 3.2 | 6.3 | 6.3 |
| 10% | 50 | 17.8 | 25 | 12.5 | 3.2 | 8.87 | 17.8 | 25 | 25 | 6.3 | 3.2 | 6.3 |
| 15% | 50 | 25 | 25 | 25 | 8.87 | 12.5 | 25 | 25 | 25 | 12.5 | 6.3 | 12.5 |
| 20% | 50 | 25 | 50 | 35.4 | 8.87 | 17.8 | 25 | —a | 25 | 25 | — | 12.5 |
| 30% | >50 | 50 | 50 | 50 | 17.8 | 25 | >50 | 50 | 25 | 50 | 25 | 25 |
| 35% | >50 | — | — | >50 | — | — | >50 | — | — | 50 | — | — |
| [Ala8,13,8]-magainin 2 amide | 12.5 | | | 6.3 | | | 12.5 | | | 3.2 | | |
| poly(5) | >50 | | | >50 | | | >50 | | | >50 | | |
| poly(6) | >50 | | | >50 | | | >50 | | | >50 | | |
| water blank | >50 | | | >50 | | | >50 | | | >50 | | |
| aq. DMF/EtOH | >50 | | | >50 | | | >50 | | | >50 | | |
| 1 (monomer) | >50 | | | >50 | | | >50 | | | >50 | | | aNot determined.

REFERENCES (1) Stone, A. *Nat. Rev. Drug Discovery* 2002, 1, 977-985.
(2) Zasloff, M. *Nature* (London, UK.) 2002, 415, 389-395.
(3) Tossi, A.; Sandri, L.; Giangaspero, A. *Biopolymers* 2000, 55, 4-30.
(4) Matsuzaki, K.; Nakamura, A.; Murase, O.; Sugishita, K.-i.; Fujii, N.; Miyajima, K. *Biochemistry* 1997, 36, 2104-2111.
(5) Bessalle, R.; Kapitkovsky, A.; Gorea, A.; Shalit, I.; Fridkin, M. *FEBS Lett.* 1990, 274, 151-155; Wade, D.; Boman, A.; Wahlin, B.; Drain, C. M.; Andreu, D.; Boman, H. G.; Merrifield, R. B. *Proc. Natl. Acad. Sci. U.S.A.* 1990, 87, 4761-4765; Merrifield, R. B.; Juvvadi, P.; Andreu, D.; Ubach, J.; Boman, A.; Boman, H. G. *Proc. Natl. Acad. Sci. U.S.A.* 1995, 92, 3449-3453.
(6) Cheng, R. P.; Gellman, S. H.; DeGrado, W. F. *Chem. Rev.* (Washington, D.C.) 2001, 101, 3219-3232; Gademann, K.; Hintermann, T.; Schreiber, J. V. *Curr. Med. Chem.* 1999, 6, 905-925.
(7) Hamuro, Y.; Schneider, J. P.; DeGrado, W. F. *J. Am. Chem. Soc.* 1999, 121, 12200-12201; Liu, D.; DeGrado, W. F. *J. Am. Chem. Soc.* 2001, 123, 7553-7559; Arvidsson, P. I.; Frackenpohl, J.; Ryder, N. S.; Liechty, B.; Petersen, F.; Zimmermann, H.; Camenisch, G. P.; Woessner, R.; Seebach, D. *ChemBioChem* 2001, 2, 771-773.
(8) Porter, E. A.; Wang, X.; Lee, H.-S.; Weisblum, B.; Gellman, S. H. *Nature* (London, U.K.) 2000, 404, 565; Raguse, T. L.; Porter, E. A.; Weisblum, B.; Gellman, S. H. *J. Am. Chem. Soc.* 2002, 124, 12774-12785.
(9) Porter, E. A.; Weisblum, B.; Gellman, S. H. *J. Am. Chem. Soc.* 2002, 124, 7324-7330.
(10) Tew, G. N.; Liu, D.; Chen, B.; Doerksen, R. J.; Kaplan, J.; Carroll, P. J.; Klein, M. L.; DeGrado, W. F. *Proc. Natl. Acad. Sci. U.S.A.* 2002, 99, 5110-5114.
(11) Giangaspero, A.; Sandri, L.; Tossi, A. *Eur J Biochem* 2001, 268, 5589-5600.
(12) Oh, T. J.; Smets, G. *J. Polym. Sci., Part C. Polym. Lett.* 1986, 24, 229-232.
(13) Pertinent data may be found in the Supporting Information.
(14) Vucetic, J. J.; Vandjel, V. H.; Janic, M. D. *Glas. Hem. Drus. Beograd* 1977, 42, 389-391; Kawabata, N.; Nishiguchi, M. *Appl. Environ. Microbiol.* 1988, 54, 2532-2535; Tiller, J. C.; Liao, C.-J.; Lewis, K.; Klibanov, A. M. *Proc. Natl. Acad. Sci. U.S.A.* 2001, 98, 5981-5985; Sheldon, B. G.; Wingard, R. E., Jr.; Weinshenker, N. M.; Dawson, D. J. In *PCT Int. Appl.;* (Dynapol, USA). Wo, 1983, p 30 pp; Chen, C. Z.; Beck-Tan, N. C.; Dhurjati, P.; Van Dyk, T. K.; LaRossa, R. A.; Cooper, S. L. *Biomacromolecules* 2000, 1, 473-480; Ohta, S.; Misawa, Y.; Miyamoto, H.; Makino, M.; Nagai, K.; Shiraishi, T.; Nakagawa, Y.; Yamato, S.; Tachikawa, E.; Zenda, H. *Biol. Pharm. Bull.* 2001, 24, 1093-1096.
(15) Ikeda, T.; Tazuke, S. *Makromol. Chem., Rapid Commun.* 1983, 4, 459-461.
(16) Ikeda, T.; Tazuke, S.; Suzuki, Y. *Makromol. Chem.* 1984, 185, 869-876.
(17) Li, G.; Shen, J.; Zhu, Y. *J. Appl. Polym. Sci.* 1998, 67, 1761-1768.
(18) Senuma, M.; Tashiro, T.; Iwakura, M.; Kaeriyama, K.; Shimura, Y. *J. Appl. Polym. Sci.* 1989, 37, 2837-2843.
(19) Senuma, M.; Iwakura, M.; Ebihara, S.; Shimura, Y.; Kaeriyama, K. *Angew. Makromol. Chem.* 1993, 204, 119-125.
(20) Lin, J.; Qiu, S.; Lewis, K.; Klibanov, A. M. *Biotechnol. Prog.* 2002, 18, 1082-1086.

(21) Yanisch-Perron, C.; Vieira, J.; Messing, J. *Gene* 1985, 33, 103-119.
(22) Young, F. E.; Smith, C.; Reilly, B. E. *J. Bacteriol.* 1969, 98, 1087-1097.
(23) Clinical isolate from the Weisblum laboratory strain collection.
(24) Nicas, T. I.; Wu, C. Y.; Hobbs, J. N., Jr.; Preston, D. A.; Allen, N. E. *Antimicrob. Agents Chemother.* 1989, 33, 1121-1124.
(25) Chen, H. C.; Brown, J. H.; Morell, J. L.; Huang, C. M. *FEBS Lett.* 1988, 236, 462-466.
(26) Matsuzaki, K.; Sugishita, K.; Harada, M.; Fujii, N.; Miyajima, K. *Biochim. Biophys. Acta* 1997, 1327, 119-130; Wieprecht, T.; Dathe, M.; Beyermann, M.; Krause, E.; Maloy, W. L.; MacDonald, D. L.; Bienert, M. *Biochemistry* 1997, 36, 6124-6132.
(27) Oren, Z.; Hong, J.; Shai, Y. *J. Biol. Chem.* 1997, 272, 14643-14649; Oren, Z.; Shai, Y. *Biochemistry* 2000, 39, 6103-6114.
(28) Doddrell, D. M., D. T. Pegg, M. R., Bendall, *J. Magn. Res.* 1982, 48, 323-327.
(29) Denisov, E. T., T. G. Denisova, T. S. Pokidova, "Handbook of Free Radical Initiators,"© 2003, Wiley, New York, N.Y.; ISBN 0-471-20753-5.
(30) Yau, W. W., J. J. Kirkland, D. D. Bly, "Modern size-exclusion liquid chromatography; practice of gel permeation and gel filtration chromatography,"© 1979, Wiley: New York, N.Y.

What is claimed is:

1. A pharmaceutical composition for treating microbial infection in a subject in need thereof, the composition comprising an antimicrobial-effective amount of a compound selected from the group consisting of a polymer of formula $-(A)_n-$, wherein each A is a residue independently selected from the group consisting of:

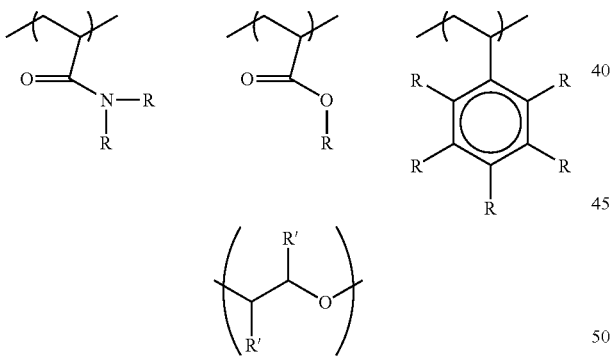

wherein each R is independently selected from the group consisting of hydrogen; linear or branched $C_1$-$C_{30}$-alkyl, alkenyl, or alkynyl; unsubstituted amino-$C_1$-$C_6$-alkyl; mono-substituted amino-$C_1$-$C_6$-alkyl; disubstituted amino-$C_1$-$C_6$-alkyl; mono- or bicyclic aryl; mono- or bicyclic heteroaryl having up to 5 heteroatoms selected from N, O, and S; mono- or bicyclic aryl-$C_1$-$C_6$-alkyl; mono- or bicyclic heteroaryl-$C_1$-$C_6$-alkyl; $-(CH_2)_{n+1}-OR^1$; $-(CH_2)_{n+1}-SR^1$; $-(CH_2)_{n+1}-S(=O)-CH_2-R^1$; $-(CH_2)_{n+1}-S(=O)_2-CH_2-R^1$; $-(CH_2)_{n+1}-NR^1R^1$; $-(CH_2)_{n+1}-NHC(=O)R^1$; $-(CH_2)_{n+1}-NHS(=O)_2-CH_2-R^1$; $-(CH_2)_{n+1}-O-(CH_2)_m-R^2$; $-(CH_2)_{n+1}-S-(CH_2)_m-R^2$; $-(CH_2)_{n+1}-S(=O)-(CH_2)_m-R^2$; $-(CH_2)_{n+1}-S(=O)_2-(CH_2)_m-R^2$; $-(CH_2)_{n+1}-NH-(CH_2)_m-R^2$; $-(CH_2)_{n+1}-N-[(CH_2)_m-R^2]_2$; $-(CH_2)_{n+1}-NHC(=O)-(CH_2)_{n+1}-R^2$; and $-(CH_2)_{n+1}-NHS(=O)_2-(CH_2)_m-R^2$;

wherein each $R^1$ is independently selected from the group consisting of hydrogen; $C_1$-$C_6$-alkyl, alkenyl, or alkynyl; mono- or bicyclic aryl; mono- or bicyclic heteroaryl having up to 5 heteroatoms selected from N, O, and S; mono- or bicyclic aryl-$C_1$-$C_6$-alkyl; and mono- or bicyclic heteroaryl-$C_1$-$C_6$-alkyl; and wherein each $R^2$ is independently selected from the group consisting of hydroxy; $C_1$-$C_6$-alkyloxy; aryloxy; heteroaryloxy; thio; $C_1$-$C_6$-alkylthio; $C_1$-$C_6$-alkylsulfinyl; $C_1$-$C_6$-alkylsulfonyl; arylthio; arylsulfinyl; arylsulfonyl; heteroarylthio; heteroarylsulfinyl; heteroarylsulfonyl; amino; mono- or di-$C_1$-$C_6$-alkylamino; mono- or diarylamino; mono- or diheteroarylamino; N-alkyl-N-arylamino; N-alkyl-N-heteroarylamino; N-aryl-N-heteroarylamino; aryl-$C_1$-$C_6$-alkylamino; carboxylic acid; carboxamide; mono- or di-$C_1$-$C_6$-alkylcarboxamide; mono- or diarylcarboxamide; mono- or diheteroarylcarboxamide; N-alkyl-N-arylcarboxamide; N-alkyl-N-heteroarylcarboxamide; N-aryl-N-heteroarylcarboxamide; sulfonic acid; sulfonamide; mono- or di-$C_1$-$C_6$-alkylsulfonamide; mono- or diarylsulfonamide; mono- or diheteroarylsulfonamide; N-alkyl-N-arylsulfonamide; N-alkyl-N-heteroarylsulfonamide; N-aryl-N-heteroarylsulfonamide; urea; mono- di- or tri-substituted urea, wherein the substitutent(s) is selected from the group consisting of $C_1$-$C_6$-alkyl, aryl, and heteroaryl; O-alkylurethane; O-arylurethane; and O-heteroarylurethane;

wherein R' is selected from same group recited above for R, provided that one R' is hydrogen;

wherein n is an integer≥6; and wherein at least one A is a residue containing a nitrogen atom, the nitrogen atom being capable of being quaternized, or a pharmaceutically suitable salt thereof;

in combination with a pharmaceutical carrier suitable for oral, rectal, topical, parenteral, nasal or bronchial administration.

2. The pharmaceutical composition of claim 1, wherein the compound has a molecular weight of between about 4.5 kDa and 11.5 kDa as determined by gel permeation chromatography.

3. The pharmaceutical composition of claim 1, wherein each R is independently selected from the group consisting of hydrogen; linear or branched $C_1$-$C_{30}$-alkyl, alkenyl, or alkynyl; unsubstituted amino-$C_1$-$C_6$-alkyl; mono-substituted amino-$C_1$-$C_6$-alkyl; disubstituted amino-$C_1$-$C_6$-alkyl; mono- or bicyclic aryl; and mono- or bicyclic heteroaryl having up to 5 heteroatoms selected from N, O, and S.

4. The pharmaceutical composition of claim 1, wherein each R is independently selected from the group consisting of mono- or bicyclic aryl-$C_1$-$C_6$-alkyl, mono- or bicyclic heteroaryl-$C_1$-$C_6$-alkyl, $-(CH_2)_{n+1}-OR^1$, $-(CH_2)_{n+1}-SR^1$, $-(CH_2)_{n+1}-S(=O)-CH_2-R^1$, $-(CH_2)_{n+1}-S(=O)_2-CH_2-R^1$, $-(CH_2)_{n+1}-NR^1R^1$, $-(CH_2)_{n+1}-NHC(=O)R^1$, $-(CH_2)_{n+1}-NHS(=O)_2-CH_2-R^1$, $-(CH_2)_{n+1}-O-(CH_2)_m-R^2$, $-(CH_2)_{n+1}-S-(CH_2)_m-R^2$, $-(CH_2)_{n+1}-S(=O)-(CH_2)_m-R^2$, $-(CH_2)_{n+1}-S(=O)_2-(CH_2)_m-R^2$, $-(CH_2)_{n+1}-NH-(CH_2)_m-R^2$, $-(CH_2)_{n+1}-N-[(CH_2)_m-R^2]_2$, $-(CH_2)_{n+1}-NHC(=O)-(CH_2)_{n+1}-R^2$, and $-(CH_2)_{n+1}-NHS(=O)_2-(CH_2)_m-R^2$.

5. The pharmaceutical composition of claim 1, wherein each $R^1$ is independently selected from the group consisting of hydrogen and $C_1$-$C_6$-alkyl, alkenyl, or alkynyl.

6. A pharmaceutical composition for treating microbial infection in a subject in need thereof, the composition comprising an antimicrobial-effective amount of a compound selected from the group consisting of a polymer of formula -(A)$_n$-, wherein each A is a residue independently selected from the group consisting of:

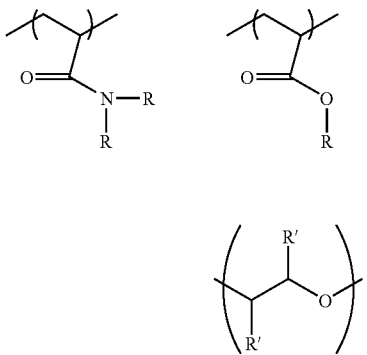

wherein each R is independently selected from the group consisting of hydrogen; linear or branched $C_1$-$C_{30}$-alkyl, alkenyl, or alkynyl; unsubstituted amino-$C_1$-$C_6$-alkyl; mono-substituted amino-$C_1$-$C_6$-alkyl; disubstituted amino-$C_1$-$C_6$-alkyl; mono- or bicyclic aryl; mono- or bicyclic heteroaryl having up to 5 heteroatoms selected from N, O, and S; mono- or bicyclic aryl-$C_1$-$C_6$-alkyl; mono- or bicyclic heteroaryl-$C_1$-$C_6$-alkyl; —(CH$_2$)$_{n+1}$—OR$^1$; —(CH$_2$)$_{n+1}$—SR$^1$; —(CH$_2$)$_{n+1}$—S(=O)—CH$_2$—R$^1$; —(CH$_2$)$_{n+1}$—S(=O)$_2$—CH$_2$—R$^1$; —(CH$_2$)$_{n+1}$—NR$^1$R$^1$; —(CH$_2$)$_{n+1}$—NHC(=O)R$^1$; —(CH$_2$)$_{n+1}$—NHS(=O)$_2$—CH$_2$—R$^1$; —(CH$_2$)$_{n+1}$—O—(CH$_2$)$_m$—R$^2$; —(CH$_2$)$_{n+1}$—S—(CH$_2$)$_m$—R$^2$; —(CH$_2$)$_{n+1}$—S(=O)—(CH$_2$)$_m$-R$^2$; —(CH$_2$)$_{n+1}$—S(=O)$_2$—(CH$_2$)$_m$—R$^2$; —(CH$_2$)$_{n+1}$—NH—(CH$_2$)$_m$—R$^2$; —(CH$_2$)$_{n+1}$—N—[(CH$_2$)$_m$—R$^2$]$_2$; —(CH$_2$)$_{n+1}$—NHC(=O)—(CH$_2$)$_{n+1}$—R$^2$; and —(CH$_2$)$_{n+1}$—NHS(=O)$_2$—(CH$_2$)$_m$—R$^2$;

wherein each R$^1$ is independently selected from the group consisting of hydrogen; $C_1$-$C_6$-alkyl, alkenyl, or alkynyl; mono- or bicyclic aryl; mono- or bicyclic heteroaryl having up to 5 heteroatoms selected from N, O, and S; mono- or bicyclic aryl-$C_1$-$C_6$-alkyl; and mono- or bicyclic heteroaryl-$C_1$-$C_6$-alkyl; and wherein each R$^2$ is independently selected from the group consisting of hydroxy; $C_1$-$C_6$-alkyloxy; aryloxy; heteroaryloxy; thio; $C_1$-$C_6$-alkylthio; $C_1$-$C_6$-alkylsulfinyl; $C_1$-$C_6$-alkylsulfonyl; arylthio; arylsulfinyl; arylsulfonyl; heteroarylthio; heteroarylsulfinyl; heteroarylsulfonyl; amino; mono- or di-$C_1$-$C_6$-alkylamino; mono- or diarylamino; mono- or diheteroarylamino; N-alkyl-N-arylamino; N-alkyl-N-heteroarylamino; N-aryl-N-heteroarylamino; aryl-$C_1$-$C_6$-alkylamino; carboxylic acid; carboxamide; mono- or di-$C_1$-$C_6$-alkylcarboxamide; mono- or diarylcarboxamide; mono- or diheteroarylcarboxamide; N-alkyl-N-arylcarboxamide; N-alkyl-N-heteroarylcarboxamide; N-aryl-N-heteroarylcarboxamide; sulfonic acid; sulfonamide; mono- or di-$C_1$-$C_6$-alkylsulfonamide; mono- or diarylsulfonamide; mono- or diheteroarylsulfonamide; N-alkyl-N-arylsulfonamide; N-alkyl-N-heteroarylsulfonamide; N-aryl-N-heteroarylsulfonamide; urea; mono- di- or tri-substituted urea, wherein the substitutent(s) is selected from the group consisting of $C_1$-$C_6$-alkyl, aryl, and heteroaryl; O-alkylurethane; O-arylurethane; and O-heteroarylurethane;

wherein R' is selected from same group recited above for R, provided that one R' is hydrogen;

wherein n is an integer≥6; and wherein at least one A is a residue containing a nitrogen atom, the nitrogen atom being capable of being quaternized, or a pharmaceutically suitable salt thereof.

7. The pharmaceutical composition of claim 1, wherein the at least one residue containing the nitrogen atom is present in the polymer in proportion with other residues at no less than about 70%.

8. A method of preventing and treating microbial infections in a subject in need thereof, the method comprising administering to the subject an effective anti-microbial amount of a pharmaceutical composition as recited in claim 6.

9. The pharmaceutical composition of claim 6, further comprising, in combination, a pharmaceutically suitable carrier.

10. The pharmaceutical composition of claim 9, wherein the pharmaceutical carrier is suitable for oral, rectal, topical, parenteral, nasal or bronchial administration.

11. The pharmaceutical composition of claim 6, wherein the compound has a molecular weight of between about 4.5 kDa and 11.5 kDa as determined by gel permeation chromatography.

12. The pharmaceutical composition of claim 6, wherein each R is independently selected from the group consisting of hydrogen; linear or branched $C_1$-$C_{30}$-alkyl, alkenyl, or alkynyl; unsubstituted amino-$C_1$-$C_6$-alkyl; mono-substituted amino-$C_1$-$C_6$-alkyl; disubstituted amino-$C_1$-$C_6$-alkyl; mono- or bicyclic aryl; and mono- or bicyclic heteroaryl having up to 5 heteroatoms selected from N, O, and S.

13. The pharmaceutical composition of claim 6, wherein each R is independently selected from the group consisting of mono- or bicyclic aryl-$C_1$-$C_6$-alkyl, mono- or bicyclic heteroaryl-$C_1$-$C_6$-alkyl, —(CH$_2$)$_{n+1}$—OR$^1$, —(CH$_2$)$_{n+1}$—SR$^1$, —(CH$_2$)$_{n+1}$—S(=O)—CH$_2$—R$^1$, —(CH$_2$)$_{n+1}$—S(=O)$_2$—CH$_2$—R$^1$, —(CH$_2$)$_{n+1}$—NR$^1$R$^1$, —(CH$_2$)$_{n+1}$—NHC(=O)R$^1$, —(CH$_2$)$_{n+1}$—NHS(=O)$_2$—CH$_2$—R$^1$, —(CH$_2$)$_{n+1}$—O—(CH$_2$)$_m$—R$^2$, —(CH$_2$)$_{n+1}$—S—(CH$_2$)$_m$—R$^2$, —(CH$_2$)$_{n+1}$—S(=O)—(CH$_2$)$_m$-R$^2$, —(CH$_2$)$_{n+1}$—S(=O)$_2$—(CH$_2$)$_m$—R$^2$, —(CH$_2$)$_{n+1}$—NH—(CH$_2$)$_m$—R$^2$, —(CH$_2$)$_{n+1}$—N—[(CH$_2$)$_m$—R$^2$]$_2$, —(CH$_2$)$_{n+1}$—NHC(=O)—(CH$_2$)$_{n+1}$—R$^2$, and —(CH$_2$)$_{n+1}$—NHS(=O)$_2$—(CH$_2$)$_m$—R$^2$.

14. The pharmaceutical composition of claim 6, wherein each R$^1$ is independently selected from the group consisting of hydrogen and $C_1$-$C_6$-alkyl, alkenyl, or alkynyl.

15. The pharmaceutical composition of claim 6, wherein the at least one residue containing the nitrogen atom is present in the polymer in proportion with other residues at no less than about 70%.

* * * * *